US008802816B2

(12) United States Patent
Hazra et al.

(10) Patent No.: US 8,802,816 B2
(45) Date of Patent: Aug. 12, 2014

(54) METHOD OF OBTAINING A PURIFIED, BIOLOGICALLY ACTIVE HETEROLOGOUS PROTEIN

(75) Inventors: Partha Hazra, Karnataka (IN); Nitesh Dave, Karnataka (IN); Vivekanandan Kannan, Karnataka (IN); Sanjay Tiwari, Karnataka (IN); Anuj Goel, Karnataka (IN); Harish Iyer, Karnataka (IN); Nita Roy, Karnataka (IN); Krishnamurthy Venkatesan, Tamil Nadu (IN); Anoop Vasudevan, Kerala (IN); Anupama Jagadish, Karnataka (IN); Goldy Sachdev, Karnataka (IN); Mukesh Babuappa Patale, Maharashtra (IN)

(73) Assignee: Biocon Limited, Bangalore (IN)

( * ) Notice: Subject to any disclaimer, the term of this patent is extended or adjusted under 35 U.S.C. 154(b) by 124 days.

(21) Appl. No.: 12/918,079

(22) PCT Filed: Apr. 3, 2008

(86) PCT No.: PCT/IN2008/000219
§ 371 (c)(1),
(2), (4) Date: Aug. 18, 2010

(87) PCT Pub. No.: WO2009/104199
PCT Pub. Date: Aug. 27, 2009

(65) Prior Publication Data
US 2011/0236925 A1    Sep. 29, 2011

(30) Foreign Application Priority Data
Feb. 19, 2008  (IN) .............................. 420/CHE/2008

(51) Int. Cl.
*A61K 38/28* (2006.01)
*C12N 15/81* (2006.01)
*C12N 15/74* (2006.01)

(52) U.S. Cl.
USPC .......... 530/303; 530/304; 530/305; 435/69.1; 435/483

(58) Field of Classification Search
None
See application file for complete search history.

(56) References Cited

U.S. PATENT DOCUMENTS

| 5,245,008 | A | * | 9/1993 | Dickhardt et al. | 530/305 |
| 5,466,666 | A | * | 11/1995 | Obermeier et al. | 514/6.2 |
| 7,445,775 | B2 | * | 11/2008 | Collen et al. | 424/93.21 |
| 2003/0104607 | A1 | * | 6/2003 | Annibali | 435/255.5 |
| 2007/0129284 | A1 | * | 6/2007 | Kjeldsen et al. | 514/3 |

OTHER PUBLICATIONS

Vajo et al., Endocrine Reviews 22: 706-717, 2001.*
Kroeff et al., J. chromatography 461, 45-61, 1989.*

* cited by examiner

*Primary Examiner* — Gyan Chandra
(74) *Attorney, Agent, or Firm* — Harness, Dickey & Pierce, PLC

(57) ABSTRACT

The invention relates to methods of separation and/or purification of impurities yielding a purified heterologous protein product devoid of related impurities or with substantially minimal quantities of such glycosylated impurities. More specifically, the invention relates to the identification of glycosylated forms of insulin analogues such as glargine impurities characterized post expression in yeast based systems such as *Pichia pastoris*. The invention also relates to methods used to clone gene encoding the protein insulin glargine; inserting the related gene in a suitable yeast host; producing culture of the recombinant strain, stimulating expression of the heterologous polypeptide, its secretion and purification post fermentation and related enzymatic conversions.

9 Claims, 9 Drawing Sheets

Enzyme treatment end (10hr)

METHOD OF OBTAINING A PURIFIED, BIOLOGICALLY ACTIVE HETEROLOGOUS PROTEIN

FIELD OF THE INVENTION

The invention relates to methods of separation and/or purification of impurities yielding a purified heterologous protein product devoid of related impurities or with substantially minimal quantities of such glycosylated impurities. More specifically, the invention relates to the identification of glycosylated forms of insulin analogs such as glargine impurities characterized post expression in yeast based systems such as *Pichia pastoris*. The invention also relates to methods used to clone gene encoding the protein insulin glargine; inserting the related gene in a suitable yeast host; producing culture of the recombinant strain, stimulating expression of the heterologous polypeptide, its secretion and purification post fermentation and related enzymatic conversions.

BACKGROUND OF THE INVENTION AND PRIOR ART

Description of Related Art

Recombinant forms of insulin, insulin analogues and/or derivatives have been produced in various microbial expression systems. Currently organisms such as *E. coli, S. cerevisiae* have been employed for the commercial production of recombinant human insulin and derivatives thereof. Owing to certain disadvantages of these systems such as low expression levels, difficulties in down stream purification etc. the use of methylotrophic yeast *Pichia pastoris* has been favored as a protein expression system. The expression system offers several advantages such as high expression, simple processing, low production cost, high density culture (U.S. Pat. No. 6,800,606).

Yeast expression systems are popular because they are easy to grow, are fast and scalable; however, some yeast expression systems have produced inconsistent results, and it is sometimes difficult to achieve high yields. One yeast expression system that has shown great promise is the methylotrophic *Pichia pastoris*. Compared to other eukaryotic expression systems, *Pichia* offers many advantages because it does not have the endotoxin problem associated with bacteria or the viral contamination problem of proteins produced in animal cell culture (Cino, Am Biotech Lab, May 1999). *Pichia's* prolific growth rate makes it easily scalable to large-scale production, although scale-up challenges include pH control, oxygen limitation, nutrient limitation, temperature fluctuation, and other safety considerations (Gottschalk, 2003, BioProcess Intl 1(4):54-61; Cino Am Biotech Lab, May 1999).

Albeit various advantages are attributed to yeast based expression systems such as *Pichia pastoris*, one of the major disadvantages of this system is the post-translational modification of resulting proteins which later exist as impurities in the final product that is difficult to purify. Although there are a number of post translational modifications of proteins known, the most common form of post translational modification is glycosylation. (Hart G. W, Glycosylation, Curr. Opin. Cell. Biol 1992; 4: 1017). Glycosylation can be either N-linked or O-linked depending on the expression system. (Gemmill T R et al., Overview of N- and O-linked oligosaccharide structures found in various yeast species, Biochemica et Biophysica Acta, 1999; 1426:227). Glycosylation affects stability of protein conformation, immunogenicity, clearance rate, protection from proteolysis and improves protein solubility. (Walsh G, Biopharmaceutical benchmarks 2006, Nature Biotechnology, 2006; 24:769).

Despite great advances in improving biotechnological manufacturing, no global solutions exist for every protein. The manufacturing process for a specific therapeutic protein requires novel and innovative solutions to problems that may be specific for that protein or family of proteins. Likewise, successful commercial applications often rely on a combination of specific properties of the protein or family of proteins, and the production processes used for manufacturing that protein or family proteins as pharmaceutical products.

The present invention relates to the identification of various glycoforms of insulin analogues more specifically insulin glargine through chemical methods coupled with mass spectrometry techniques such as electrospray and matrix assisted laser desorption ionisation for identification. The invention shall herewith permit selective purification of the product from the aforesaid impurities through optimized down stream purification methods attributed to the better understanding of the nature of impurities present in the final product. The end product thus purified shall be substantially free of impurities characterized in the instant invention.

U.S. Pat. No. 4,444,683 and its related applications claim glycosylated insulins, wherein glucose or mannose that is coupled with insulin via a spacer group derived from dicarboxylic acids, acid anhydrides or phenyl amines or a combination thereof.

WO 90/10645 specifically claims glycosylated insulin containing one or more monosaccharide groups or one ore more oligosaccharide groups with up to 3 sugar units. Monoglycosylated or triglycosylated insulins at positions A1, B1 or B29.

WO 99/52934 claims a process of separating glycosylated proteins from non-glycosylated proteins by subjecting a solution comprising glycosylated and non-glycosylated proteins to chromatography using a $Ca^{++}$ containing eluent, and obtaining a fraction comprising non-glycosylated proteins, said fraction substantially free from glycosylated proteins.

Glycoforms of Glargine are not disclosed in any of the foregoing prior art. The invention discusses the methods of purifying insulin analogues such as insulin glargine with reduced levels of these characterized glycosylated impurities to obtain a 100% pure glargine product after fermentation through yeast based expression systems.

OBJECTS OF THE INVENTION

The main object of the present invention is to develop a method of obtaining a purified, biologically active heterologous protein recombinantly expressed in a yeast expression system, characterized in that said purified protein is devoid of or contains substantially minimal amounts of glycosylated byproducts.

Another object of the present invention is to develop a process of obtaining a purified, biologically active heterologous protein recombinantly expressed in a host cell.

Yet another object of the present invention is to develop a process of producing a purified, biologically active heterologous protein.

Still another object of the present invention is to obtain a purified, biologically active heterologous protein product with purity of at least 96%.

Still another object of the present invention is to obtain a purified, biologically active heterologous protein product with purity in the range of 97-100%.

Still another object of the present invention is to obtain a purified insulin glargine with purity of at least 96%.

Still another object of the present invention is to obtain a purified insulin glargine containing less than 1% of glycosylated impurities.

Still another object of the present invention is to obtain a purified insulin glargine devoid of glycosylated impurities.

Still another object of the present invention is to obtain a purified insulin glargine devoid of glycosylated impurities, wherein the glycosylated form of the protein may be monoglycosylated, triglycosylated or polyglycosylated.

STATEMENT OF THE INVENTION

Accordingly, the present invention relates to a method of obtaining a purified, biologically active heterologous protein recombinantly expressed in a yeast expression system, characterized in that said purified protein is devoid of or contains substantially minimal amounts of glycosylated byproducts; a process of obtaining a purified, biologically active heterologous protein recombinantly expressed in a host cell which process comprises steps of: a) Culturing host cells transformed by a vector containing a DNA sequence defined by formula I encoding the heterologous protein under conditions suitable for the expression of the protein; b) Recovery of the expressed protein comprising separating the said protein from host cells to produce a recovered protein preparation; c) Subjecting the recovered protein of step (b) to a step of crystallization; d) Performing a step of enzymatic conversion in the presence of trypsin or trypsin like enzyme; e) Purifying the said protein containing at least one related impurity comprising contacting the said protein mixture with a chromatographic matrix wherein purification is carried out employing a polar organic buffer solvent, in an aqueous phase containing an organic acid buffer; and f) Precipitating the eluted protein; a process of producing a purified, biologically active heterologous protein of claim 9 which comprises: a) Inoculating an aqueous fermentation medium with a transformant yeast strain harboring an expression vector which directs the expression of the said protein; and b) Growing the transformed strain in the fermentation medium under conditions effective for expression of said protein; a purified, biologically active heterologous protein with purity of at least 96%; a purified, biologically active heterologous protein product with purity in the range of 97-100%; purified insulin glargine with purity of at least 96%; purified insulin glargine containing less than 1% of glycosylated impurities; purified insulin glargine devoid of glycosylated impurities; and purified insulin glargine wherein the glycosylated form of the protein may be monoglycosylated, triglycosylated or polyglycosylated.

DESCRIPTION OF PREFERRED EMBODIMENTS

Figure 1:
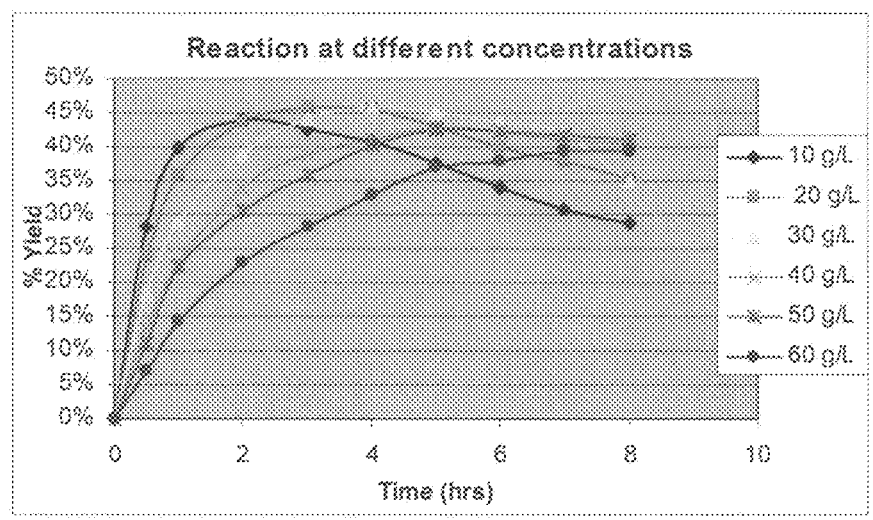
FIG. 1: Graph of % yield versus Time (hrs) of trypisinised Insulin glargine and reaction at different concentrations.

The present invention relates to a method of obtaining a purified, biologically active heterologous protein recombinantly expressed in a yeast expression system, characterized in that said purified protein is devoid of or contains substantially minimal amounts of glycosylated byproducts.

In another embodiment of the present invention, the DNA encoding a heterologous protein as represented by formula I

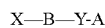

wherein,

X is a leader peptide sequence comprising at least one amino acid.

B is the amino acid sequence of the B chain of the insulin molecule, its derivatives or analogs.

Y is a linker peptide comprising at least two amino acids.

A is the amino acid sequence of the A chain of the insulin molecule, its derivatives or analogs and the A and B chain can be modified by amino acid substitution, deletion and/or additions.

In yet another embodiment of the present invention, the linker peptide may be any sequence comprising at least two amino acids with the provision that the first two amino acids represent "RR"

In still another embodiment of the present invention, said protein is defined by SEQ ID: 1 or SEQ ID: 2.

In still another embodiment of the present invention, the host cell of the yeast expression system is selected from *Pichia* sp.

In still another embodiment of the present invention, the host cell of the yeast expression system is selected from the group comprising *Pichia pastoris, Pichia methanolica, Saccharomyces cerevisiae, Schisaosaccharomyces pombe, Yarrovia lipilitica, Hansenula polymorpha, Kluyveromyces lactis*.

In still another embodiment of the present invention, the glycosylated form of the protein may be monoglycosylated, triglycosylated or polyglycosylated.

In still another embodiment of the present invention, said purified protein contains less than 1% of glycosylated impurities.

The present invention also relates to a process of obtaining a purified, biologically active heterologous protein recombinantly expressed in a host cell which process comprises steps of:
  a) Culturing host cells transformed by a vector containing a DNA sequence defined by formula I encoding the heterologous protein under conditions suitable for the expression of the protein;
  b) Recovery of the expressed protein comprising separating the said protein from host cells to produce a recovered protein preparation;
  c) Subjecting the recovered protein of step (b) to a step of crystallization;
  d) Performing a step of enzymatic conversion in the presence of trypsin or trypsin like enzyme;
  e) Purifying the said protein containing at least one related impurity comprising contacting the said protein mixture with a chromatographic matrix wherein purification is carried out employing a polar organic buffer solvent, in an aqueous phase containing an organic acid buffer; and
  f) Precipitating the eluted protein.

In yet another embodiment of the present invention, the DNA encoding a heterologous protein is represented by formula I

wherein,
X is a leader peptide sequence comprising at least one amino acid.
B is the amino acid sequence of the B chain of the insulin molecule, its derivatives or analogs
Y is a linker peptide comprising at least two amino acids.
A is the amino acid sequence of the A chain of the insulin molecule, its derivatives or analogs and the A and B chain can be modified by amino acid substitution, deletion and/or addition.

In still another embodiment of the present invention, the linker peptide may be any sequence comprising at least two amino acids with the provision that the first two aminoacids represent "RR".

In still another embodiment of the present invention, the gene defined by SEQ ID 1 or 2 is cloned in frame with a signal peptide.

In still another embodiment of the present invention, the gene defined by SEQ ID 1 or 2 is cloned in frame with mat-α-signal peptide.

In still another embodiment of the present invention, the host cell is selected from *Pichia* sp.

In still another embodiment of the present invention, the host cell is selected from the group comprising *Pichia pastoris, Pichia methanolica, Saccharomyces cerevisiae, Schisaosaccharomyces pombe, Yarrovia lipilitica, Hansenula polymorpha, Kluyveromyces lactis*.

In still another embodiment of the present invention, the host cell is *Pichia pastoris*.

In still another embodiment of the present invention, the host strain is GS115.

The present invention also relates to a process of producing a purified, biologically active heterologous protein which comprises:
  a) Inoculating an aqueous fermentation medium with a transformant yeast strain harboring an expression vector which directs the expression of the said protein; and
  b) Growing the transformed strain in the fermentation medium under conditions effective for expression of said protein.

The present invention also relates to a process of producing a purified biologically active heterologous protein wherein the expressed protein is captured from the fermentation broth using ion-exchange chromatography.

In still another embodiment of the present invention, said process comprising a step of crystallizing the protein by addition of zinc chloride and phenol.

The present invention also relates to a process of producing a purified, biologically active heterologous protein, said process comprising a step of enzymatic conversion effected in the presence of trypsin in a water-miscible organic solvent.

In still another embodiment of the present invention, the water-miscible organic solvent is selected from the group comprising DMSO, DMF, ethanol, acetone, acetonitrile, ethyl acetate or mixtures thereof.

In still another embodiment of the present invention, said process comprising a step of RP-HPLC purification of the protein mixture containing at least one related impurity by contacting the said protein mixture with a chromatographic resin matrix wherein purification is carried out employing a polar organic buffer solvent, in an aqueous phase containing an organic acid buffer.

In still another embodiment of the present invention, the polar buffer solvent is acetonitrile.

In still another embodiment of the present invention, the organic acid buffer is selected from the group comprising citric acid, acetic acid, boric acid, formic acid, hydrochloric acid and phosphoric acid.

The present invention also relates to a purified, biologically active heterologous protein product obtained according to any of the preceding claims, with purity of at least 96%.

The present invention also relates to a process a purified, biologically active heterologous protein product with purity in the range of 97-100%.

In still another embodiment of the present invention, purified insulin glargine with purity of at least 96%.

In still another embodiment of the present invention, purified insulin glargine containing less than 1% of glycosylated impurities.

In still another embodiment of the present invention, purified insulin glargine devoid of glycosylated impurities.

In still another embodiment of the present invention, purified insulin glargine wherein the glycosylated form of the protein may be monoglycosylated, triglycosylated or polyglycosylated.

Reference will now be made in detail to the presently preferred embodiments of the invention which, together with the following example, serve to explain the principles of the invention.

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems. Such methods are well known to those of ordinary skill in the art and are described in numerous publications including by way of examples.

According to one aspect of the invention, a process of obtaining a purified, biologically active heterologous protein recombinantly expressed in a host cell which method comprises steps of:
  a) Culturing host cells transformed by a vector containing a DNA sequence defined by SEQ ID 1 or 2 encoding the heterologous protein under conditions suitable for the expression of the protein.
  b) Recovery of the expressed protein comprising separating the said protein from host cells to produce a recovered protein preparation
  c) Subjecting the recovered protein of step (b) to a step of crystallisation
  d) Performing a step of enzymatic conversion in the presence of trypsin or trypsin like enzyme.
  e) Purifying the said protein containing at least one related impurity comprising contacting the said protein mixture with a chromatographic matrix wherein purification is carried out employing a polar organic buffer solvent, in an aqueous phase containing an organic acid buffer.
  f) Precipitating the eluted protein.

DEFINITIONS

"Cells" or "cell cultures" or "recombinant host cells" or "host cells" are often used interchangeably as will be clear from the context. These terms include the immediate subject cell which expresses the desired protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell.

As used herein, the term "vector" refers to a nucleic acid molecule capable of transporting another nucleic acid to which it has been linked. The term "expression vector" includes plasmids, cosmids or phages capable of synthesizing the subject proteins encoded by their respective recombinant genes carried by the vector. Preferred vectors are those capable of autonomous replication and/or expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

Polypeptides referred to herein as possessing the activity of insulin glargine, e.g. are insulin glargine are understood to have an amino acid sequence with two changes of the human insulin structure: substitution of the amino acid glycine for the native asparagine at position A21 of the A-chain of human insulin and the addition of two arginine molecules to the NH2-terminal end of the B-chain of human insulin produced by recombinant DNA technology The primary action of any insulin, including insulin glargine, is regulation of glucose metabolism. Insulin and its analogs lower blood glucose levels by stimulation of peripheral glucose uptake, especially within skeletal muscle and fat, and by inhibition of hepatic glucose production.

The DNA encoding a heterologous protein as represented by formula I

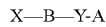

wherein,
X is a leader peptide sequence comprising at least one amino acid.
B is the amino acid sequence of the B chain of the insulin molecule, its derivatives or analogs
Y is a linker peptide comprising at least one amino acid.
A is the amino acid sequence of the A chain of the insulin molecule, its derivatives or analogs and the A and B chain can be modified by amino acid substitution, deletion and/or additions.

The term "C-peptide" or "linker peptide" as used herein includes all forms of insulin C-peptide, including native or synthetic peptides. Such insulin C-peptides may be human peptides, or may be from other animal species and genera, preferably mammals. Thus variants and modifications of native insulin C-peptide are included as long as they retain insulin C-peptide activity. It is known in the art to modify the sequences of proteins or peptides, whilst retaining their useful activity and this may be achieved using techniques which are standard in the art and widely described in the literature e.g. random or site-directed mutagenesis, cleavage and ligation of nucleic acids etc. Thus, functionally equivalent variants or derivatives of native insulin C-peptide sequences may readily be prepared according to techniques well known in the art, and include peptide sequences having a functional, e.g. a biological, activity of a native insulin C-peptide. All such analogues, variants, derivatives or fragments of insulin C-peptide are especially included in the scope of this invention, and are subsumed under the term "an insulin C-peptide".

The linker sequence can be any sequence having at least two amino acids The linker region may comprise from 2 to 25, 2 to 15, 2 to 12 or 2 to 10 amino residues, although the length is not critical and may be selected for convenience or according to choice.

The linker peptide may be any sequence comprising at least two amino acids under the provision that the first two amino acids represent "RR". Moreover, it will be generally appreciated that, under certain circumstances, it will be advantageous to provide homologs of forms of the subject insulin glargine protein which are either agonists or antagonists of only a subset of that protein's biological activities. Thus, specific biological effects can be elicited by treatment with a homolog of limited function, and with fewer side effects.

In one embodiment, the nucleic acid of the invention encodes a polypeptide which is either an agonist or antagonist the human insulin glargine protein and comprises an amino acid sequence represented by SEQ ID No: 2. Preferred nucleic acids encode a peptide having an insulin glargine protein activity and being at least 90% homologous, more preferably 95% homologous and most preferably 97% homologous with an amino acid sequence shown in SEQ ID No: 2. Nucleic acids which encode agonist or antagonist forms of insulin glargine protein and having at least about 98-99% homology with a sequence shown in SEQ ID No: 2 are also within the scope of the invention. Preferably, the nucleic acid is a cDNA molecule comprising at least a portion of the nucleotide sequence encoding an insulin glargine protein shown in SEQ ID No. 1.

The "operational elements," as discussed herein, include at least one promoter, at least one operator, at least one leader sequence, at least one Shine-Dalgarno sequence, at least one terminator codon, and any other DNA sequences necessary or preferred for appropriate transcription and subsequent translation of the vector DNA. In particular, it is contemplated that such vectors will contain at least one origin of replication recognized by the host microorganism along with at least one selectable marker and at least one promoter sequence capable of initiating transcription of the synthetic DNA sequence. It is additionally preferred that the vector, in one embodiment, contains certain DNA sequences capable of functioning as regulators, and other DNA sequences capable of coding for regulator protein. These regulators, in one embodiment, serve to prevent expression of the DNA sequence in the presence of certain environmental conditions and, in the presence of other environmental conditions, allow transcription and subsequent expression of the protein coded for by the DNA sequence.

Additionally, it is preferred that an appropriate secretory leader sequence be present, either in the vector or at the 5' end of the DNA sequence. The leader sequence is in a position which allows the leader sequence to be immediately adjacent to the initial portion of the nucleotide sequence capable of directing expression of the desired protein inhibitor without any intervening translation termination signals. The presence of the leader sequence is desired in part for one or more of the following reasons:
1) the presence of the leader sequence may facilitate host processing of the initial product to the mature recombinant protein product;
2) the presence of the leader sequence may facilitate purification of the recombinant protein product, through directing the protease inhibitor out of the cell cytoplasm;
3) the presence of the leader sequence may affect the ability of the recombinant protein product to fold to its active structure through directing the protein out of the cell cytoplasm.

"Transcriptional regulatory sequence" is a generic term used throughout the specification to refer to DNA sequences, such as initiation signals, enhancers, and promoters which induce or control transcription of protein coding sequences with which they are operably linked. In preferred embodiments, transcription of a recombinant insulin glargine gene is under the control of a promoter sequence (or other transcriptional regulatory sequence) which controls the expression of the recombinant gene in a cell-type in which expression is intended.

"Control sequences" refers to DNA sequences necessary for the expression of an operably linked coding sequence in a particular host organism. The control sequences which are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Transformation" means introducing DNA into an organism so that the DNA is replicable, either as an extra chromosomal element or by chromosomal integration.

Depending on the host cell used, transformation is done using standard techniques appropriate to such cells. General aspects of mammalian cell host system transformations have been described by Axel in U.S. Pat. No. 4,399,216 issued Aug. 16, 1983. Transformations into yeast are typically carried out according to the method of Van Solingen, P., et al., J. Bact., 130: 946 (1977) and Hsiao, C. L., et al., Proc. Natl. Acad. Sci. (USA) 76: 3829 (1979).

A recombinant expression system is selected from prokaryotic and eukaryotic hosts. Eucaryotic hosts include yeast cells (e.g., *Saccharomyces cerevisiae* or *Pichia pastoris*), mammalian cells or plant cells. Bacterial and eukaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells. The choice of the expression system depends on the features desired for the expressed polypeptide.

Consequently, the subject of the present invention is a expression system or cassette which is functional in a cell derived from a yeast selected from the group consisting of strain *Pichia* especially selected from the group consisting of *Pichia pastoris, Pichia methanolica* and *Schizosaccharomyces pombe* and allowing the expression of the desired polypeptide thereof encoding the protein fragments thereof, placed under the control of the elements necessary for its expression.

The term "recombinant", as used herein to describe a protein or polypeptide means a polypeptide produced by expression of a recombinant polynucleotide. The term "recombinant", as used herein in reference to cells, means cells that can be or have been used as recipients for recombinant vectors or other transfer DNA, and include progeny of the original cell which has been transfected. It shall be understood that progeny of a single parental cell may not be completely identical in morphology or in genomic or total DNA complement to the original parent, due to accidental or deliberate mutation. Progeny of a parental cell which are sufficiently similar to the parent to be characterized by a relevant property, such as the presence of a nucleotide sequence encoding a desired polypeptide, are also considered progeny.

A "gene of interest" (GOI) is any nucleic acid sequence for which increased transcriptional expression is desired. The GOI may encode a functional nucleic acid molecule (e.g., an RNA, such as an antisense RNA molecule) or, more typically, encodes a peptide, polypeptide or protein for which increased production is desired. The vectors of the invention can be used to express a "heterologous" protein. As used herein, the term "heterologous" means a nucleic acid sequence or polypeptide that originates from a foreign species, or that is substantially modified from its original form if from the same species. Furthermore, a modified or unmodified nucleic acid sequence or polypeptide that is not normally expressed in a cell is considered heterologous. Vectors of the invention can have one or more GOIs, inserted at the same or different insertion site, where each GOI is operably linked to a regulatory nucleic acid sequence which allows expression of the GOI.

The term "purifying" a peptide from a composition comprising the peptide and one or more contaminants thereby increasing the degree of purity of the peptide in the composition by reducing the contents of at least one contaminant from the peptide composition. More specifically the purification process of the present invention results in a biologically active heterologous protein recombinantly expressed in a yeast expression system, characterized in that said purified protein is devoid of or contains substantially minimal amounts of glycosylated byproducts.

Apart from the glycosyalated form presence of nonpolar impurity was confirmed by MALDI (m/Z: 6089). The presence of this nonpolar impurity varies from 0-0.5% in the final product which is generated during the processing of Glargine. The difference in mass between glargine (m/z: 6063) and non-polar impurities (m/z: 6089) is 26 units. Chemical identity based on molecular mass indicates the probability of water loss in one of the amino acids and acetylation The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "High Performance liquid chromatography", as used herein, refers to that chromatographic procedure in which the particles (stationary phase) used in the column packing are small (between 3 and 50 microns) and regular with little variation from the selected size. Such chromatography typically employs relatively high (around 500-3500 psi) inlet pressures.

After a host organism has been chosen, the vector is transferred into the host organism using methods generally known by those of ordinary skill in the art. Examples of such methods may be found in Advanced Bacterial Genetics by R. W. Davis et. al., Cold Spring Harbor Press, Cold Spring Harbor, N.Y., (1980), which is specifically incorporated herein by reference. It is preferred, in one embodiment, that the transformation occur at low temperatures, temperature regulation is contemplated as a means of regulating gene expression through the use of operational elements as set forth.

The host microorganisms are cultured under conditions appropriate for the expression of the insulin glargine precursor. These conditions are generally specific for the host organism, and are readily determined by one of ordinary skill in the art, in light of the published literature regarding the growth conditions for such organisms, for example Bergey's Manual of Determinative Bacteriology, 8th Ed., Williams & Wilkins Company, Baltimore, Md., which is specifically incorporated herein by reference.

Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase.

According to one aspect of the invention, Insulin glargine precursor of formula X— Glargine B chain [B1-B30]-Y-

Glargine A chain [A1-A21], wherein X is the leader sequence, B chain is the Glargine B chain sequence of B 1-B30, Y is a linker peptide sequence between B chain and A chain, A chain is the A chain of Glargine. The GIP-A precursor may be produced by expression in a host expression system not including bacteria other than *E. coli*, yeast such as *Saccharomyces* and *Kluyveromyces* for which methods are known to those skilled in the art (Methods in Enzymology vol. 194); and fungi such as *Aspergillus, Neurospora* and *Trichoderma* for which methods are known to those skilled in the art, as described in Applied Molecular Genetics of Fungi, Peberdy, Caten, Ogden, and Bennett, eds. (Cambridge University Press, N.Y. 1991), many of which can be obtained from the American Type Culture Collection, Rockville, Md., which are routinely used by those skilled in the art. Preferably, the host strain is selected from the group comprising yeast such as *Saccharomyces cerevisiae, Schisaosaccharomyces pombe, Yarrovia lipilitica, Hansenula polymorpha, Kluyveromyces lactis, Pichia methanolica* and *Pichia pastoris*, which are capable of expressing high levels of a recombinant protein. Even more preferably, the host strain is *Pichia pastoris*.

In particular, the present invention provides a process for manufacture of insulin glargine protein including a fermentation process, a recovery process, and a purification process. The process provided herein includes a fermentation process wherein the aforesaid protein is produced in *Pichia pastoris* having at least one sequence encoding the said protein is integrated into the genome, wherein the fermentation process includes a seed fermentation to grow host cells to a desired cell density and a production fermentation process comprising glycerol batch fermentation, methanol induction fermentation and finally production.

The Glargine precursor is then captured from the fermentation broth using cation-exchange chromatography. The recovery process provided herein permits capture of the glargine precursor and removal of cells and cellular debris, where the recovery process provided herein provides for a yield of 95%. Alternately, one skilled in art can test and evaluate alternate methods for capturing the desired protein product and removing cells and cellular debris including but not limited to various other chromatographic methods, centrifugation, filtration, differential precipitation, and other methods to be determined.

The glargine precursor captured from the fermentation broth is further subjected to crystallization for color removal and storage. The precipitation of the precursor in a crystallized form is suitably performed in an aqueous vehicle at a pH comprised between 3.0 and 8.0, preferably 4.0 and 6.0, most preferably at a pH of 4.0 to 5.0, the concentration of the protein in the aqueous vehicle being comprised between 1 and 80 g/L, preferably between 2 and 50 g/L, most preferably 8 to 14 g/L. The crystallisation process can be done at a temperature between 2 and 30° C. The precursor crystals can be separated from the supernatant either by centrifugation, decantation or filtration.

Crystallization of the Glargine precursor GIP-A removes the impurities carried through from the fermentation broth into the cation-exchange elution pool as well as ammonium acetate salt which is used to elute the product from the chromatography. A pure crystalline precursor also helps in reducing cost in the subsequent steps and increase the efficiency of the reaction. The crystalline form can be frozen and stored which would be subsequently stable for the multiple days when stored at −20° C.

Glargine can be prepared from the Glargine precursor through an enzymatic conversion. The conversion is effected by the presence of trypsin or trypsin like enzymes of plant, animal or microbial origin. The reaction is carried out preferably in the presence of water-miscible organic solvents like DMSO (dimethyl sulfoxide) DMF (dimethyl formamide), ethanol, acetone, acetonitrile or ethyl acetate especially DMF and DMSO. The preferable ratio of the organic solvent is about 0-65%, especially about 40-60% of the reaction mixture.

Glargine is produced by treating the precursor GIP-A with Trypsin. The leader (if present) will be cleaved from the precursor by Trypsin. The Trypsin reaction is controlled in such a way that cleavage at the C-terminal of "RR" C-peptide is maximized. But the reaction could not eliminate the unwanted cleavage by trypsin in other trypsin cleavage sites. The probable other trypsin cleavage sites are between "RR" and C-terminus of B-22 (Arg).

The rationale for the use of organic solvents should be determined by the solubility of the starting materials, tendency of enzymes to denature and its hydrolysing activity. As may be appreciated by a skilled artisan, mixtures of organic solvents may also be used. The addition of organic solvents lowers the aqueous concentration of the reaction mixture, resulting in prevention of hydrolysis of product, and also remarkably increases the solubility of the products.

The concentration of the precursor is generally about 5-50 g/L. The reaction is carried out at about pH 5 to 12, preferably about pH 8 to 10. Reaction temperature is about 0-40° C. preferably about 2-25° C. Trishydroxylmethylaminomethane (TRIS) or other buffer systems can be used at different ionic strengths to maintain the required pH. Reaction time is variable and is affected by other reaction conditions. Reaction may be continued until the purity of the product starts decreasing due to hydrolysis of the product, It takes generally about 30 minutes to 24 hours and in most cases about 4-10 hours.

The concentration of enzyme is determined depending on concentration of substrates and enzyme activity. For example, the crystalline trypsin available in the market is used preferably in a concentration about 10-100 mg/L of the reaction mixture.

The purification method comprises subjecting the insulin glargine sample to a step of purification through reverse-phase chromatography comprising a polymer based resin matrix under chromatographic conditions sufficient for obtaining said peptide of nearly 98-99% purity, preferably 100% purity.

Thus, unwanted product related impurities formed which is purified in the successive reverse phase chromatography to generate pure Glargine. Glycosylated (mono and Tri) impurities can only be detected after the first purification steps. So, special cares were taken to purify the Glycosylated impurities in the 2nd RP-HPLC purification step. The Glycosylated impurities generated during the fermentation is fully characterised and finally purified from the final product to the maximum extent.

The invention features, in a significant aspect, a method of purifying the protein, the method including the steps of subjecting the instant protein to a reverse phase HPLC column and eluting a sample that includes the peptide with an organic solvent, under conditions that allow the compound to be bound to the resin, and washing the organic solvent from the resin with an aqueous buffer solution. The effective performance of the present invention requires the individuation of right combination of the chromatographic matrix to be used, the pH value and the ionic strength of the buffer for efficient purifications Every attribute of the chromatographic procedure has a significant role to play in obtaining the desired protein product. A suitable matrix used in the chromatographic column is C8 Daisogel.

According to one aspect of the invention the yield of the purified insulin glargine product is 75%-80%, according to another aspect of the invention the yield of the purified insulin glargine product is 80%-85%, according to yet another aspect of the invention the yield of the purified insulin glargine product is 85%-90%, according to yet another aspect of the invention the yield of the purified insulin glargine product is 90%-95%, according to still another aspect of the invention the yield of the purified insulin glargine product is 95%-100%.

According to one aspect of the invention the purified insulin glargine product is devoid of or contains substantially minimal amounts of glycosylated byproducts. According to one aspect of the invention the purity of the purified insulin glargine product is at least 96%, according to another aspect of the invention the purity of the purified insulin glargine product is at least 97%, according to yet another aspect of the invention the purity of the purified insulin glargine product is at least 98%, according to yet another aspect of the invention the purity of the purified insulin glargine product is at least 99%, according to still another aspect of the invention the yield of the purified insulin glargine product is 100%.

The invention is further elaborated with the help of following examples. However, these examples should not be construed to limit the scope of the invention.

EXAMPLES

Example 1

GIP-A represent the Glargine precursor of Formula X-[Glargine B chain (B1-B30)]-Y-[Glargine A chain (A1-A21)], where X is a leader peptide sequence, B chain is Glargine B chain sequence of B1-B30, Y is a linker peptide sequence between B chain and A chain, A chain is the A-chain of Glargine. The sequence may be devoid of leader or other leader peptide. The linker peptide Y can be anyone from the example RR, RRDADDR (SEQ ID 3). The GIP-A precursor may be produced by any suitable expression system such as *Escherichia coli, Pichia pastoris, Saccharomyces cerevisiae*, CHO cells etc.

The GIP-A precursor was cloned in frame with the Mat-alfa signal peptide in *Pichia* expression vector, pPIC9K. *Pichia pastoris* host strain GS115 was transformed with the recombinant plasmid to obtain clone expressing Glargine precursor. The secreted precursor was treated with trypsin to prepare Glargine and other product related impurities. Glargine was purified by using revere phase chromatography.

SEQ ID 1 represents the sequence for the glargine precursor, having a predicted molecular weight of 6045 Da and estimated pI value of 6.88. The sequence has 159 nucleotides and 53 amino acids.

SEQ ID 2 represents the sequence for expression in *Pichia pastoris* with a predicted molecular weight of 6428.4 da, and estimated pI value of 7.78. The sequence has 171 nucleotides and 57 amino acids.

SEQ ID 3 represents the peptide sequence RRDADDR.

Glargine precursor GIP-A is secreted by *Pichia pastoris* into the culture medium. The broth is centrifuged and cells are separated from the supernatant. There are multiple options available for the capture of the precursor GIP-A including Ion-Exchange chromatography and Hydrophobic chromatography. For this invention cation-exchange chromatography and HIC were used to capture the GIP-A.

Example 2

Construction of the Recombinant Vector Carrying the Insulin Glargine Precursor Gene Insulin Glargine Precursor (GIP-A) was cloned in frame with the mat α-signal peptide in the *Pichia pastoris* expression vector, pPIC9K. The recombinant plasmid was used to transform *Pichia pastoris* host strain, GS115, and the secreted GIP-A was Insulin-Glargine Precursor which will be taken to downstream purification process to make the final product.

Transformation of a *Pichia* Host with the Recombinant Vectors Carrying the Insulin Glargine Precursor Gene:

pPIC9K/IGP-A clone harboring recombinant plasmid DNA was digested with Bgl II and used to transform electrocompetent cells of *P. pastoris* GS115 (his4) host. The invitrogen manual provides a detailed protocol of the transformation procedure.

Screening for Multi-Copy Integrants:

Approximately 2000 transformants were inoculated in YPD broth in 384 well micro titer plates along with appropriate controls. The plates were incubated at 30° C. for 24 hours and then stamped onto YPD agar plates containing 0.5 mg/mL Geniticin (G418). 49 clones were selected which were stamped further on plates 1, 2 and 3 mg/mL of G418 for second round of screening. Finally, seven clones resistant to 1-3 mgl/ml G418 were selected and used in expression studies.

Confirmation of Gene Integration in the Genome by PCR:

Genomic DNA from selected recombinant *Pichia* clones was subjected to PCR using gene specific primers in order to confirm the integration of GIP-A in the genome.

Small Scale Expression Studies in *P. pastoris*

Small scale expression studies in *P. pastoris* were carried out as per the protocol given in Invitrogen manual. Briefly, the clones were grown at 30° C. in BMGY followed by induction with methanol in BMMY at 24° C. Induction with methanol was carried out for a total of 3 days.

Example 3

Fermentation Procedure

Recombinant Insulin-Glargine fermentation process has been optimized at laboratory scale. Presented below is a brief description of the process.

Seed Preparation

The seed medium contains following ingredients: Yeast nitrogen base, Ammonium sulfate, Glycerol, potassium dihydrogen phosphate and dipotassium hydrogen phosphate and D-Biotin.

A single vial from freezer was used to inoculate the seed flask. The vials were thawed to ambient temperature before inoculation under sterile conditions. The inoculum was dispensed in the Minimal Glycerol (MGY) medium in an aseptic manner.

The quantity to be added to each flask was ascertained, such that the initial OD600 in the pre-seed flask was between 0.1-0.2. The flasks were then incubated for 20-24 h on shaker at 30° C. at a speed of 230 RPM.

Fermenter Batching Conditions

Fermentation process has two phases, Growth phase (to build up biomass) followed by induction phase. Product was formed and secreted out to the broth during methanol fed batch phase. Fermentation was performed in an in situ sterilisable fermenter. The fermentation medium comprises of, orthophosphoric acid, potassium sulphate, potassium hydroxide, magnesium sulphate calcium sulphate and glycerol. These chemicals were dissolved in potable water in the fermenter vessel and sterilized at a set point of 121° C. for a specified period. Stock solution of trace salt and biotin were prepared separately and filter sterilized and added aseptically to the fermenter after medium sterilization and pH adjustment to 5.0 with ammonium hydroxide.

Production/Fermentation procedure were adopted. The fermenter was inoculated with 5% seed inoculum from a seed shake flask. Following parameters set at the beginning of fermentation: pH: 5.0, Temperature: 30° C., DO2: 30%.

Example 4

Related Conversions and Purification Method

Insulin glargine precursor that was produced in fermentation of *Pichia pastoris* was subjected to purification the steps which involved in the purification process are as follows.

The column packed with SP Sepharose fast flow matrix (GE Biosciences) was equilibrated with 50 mM acetic acid. The cell free supernatant, adjusted to pH 3.8 using ortho phosphoric acid, was loaded on cation exchange column. The loading on the column was <50 g/L. The elution was performed using ammonium acetate. The recovery of the step was 95% at <50 g/L loading.

Precursor Crystallisation

The Glargine precursor captured from the fermentation broth by using a cation-exchange chromatography step was crystallised for the purpose of colour removal and storage. The crystallisation was done such that the precursor concentration at the start of crystallisation was around 2 to 20 g/L, preferably 8 to 14 g/L. The crystallisation was done by adding ZnCl2 & phenol and then adjusting the pH to between 3.0 and 8.0, preferably between 3.5 and 5.5. Phenol can be added at 0.1 to 0.5% of the CIEX elution pool volume. A 4% ZnCl2 solution can be added at 3 to 15% of the CIEX elution pool volume. The pH can be adjusted by using any alkali, preferably NaOH or TRIS. The crystallisation process can be done at a temperature between 2 and 30° C. and the slurry is stored for some time so that the crystals will be formed completely. The precursor crystals can be separated from the supernatant by either centrifugation or decantation.

Example 4a 463 ml of elution pool (precursor concentration 13.8 g/L) was taken and 2.315 ml of phenol (0.5% of EP volume) was added after proper thawing. This was followed by addition of 57.875 ml of 4% ZnCl2 solution (12.5% of EP volume). The pH was 4.08 at this stage and it was adjusted to 4.8 by adding 420 ml of 2.5N NaOH. The mother liquor was kept under slow stifling conditions for 15 minutes and then transferred to cold room (2-8° C.), where it was kept overnight. Then the whole mixture was centrifuged at 5000 rpm for 20 minutes in a Beckman Coulter Avanti J-26 XP centrifuge. The loss in supernatant was 1.55%.

Example 4b 500 ml of elution pool (precursor concentration 2.9 g/L) was taken and 0.625 ml of phenol (0.125% of EP volume) was added after proper thawing. This was followed by addition of 15.625 ml of 4% ZnCl2 solution (3.125% of EP volume). The pH was 4.08 at this stage and it was adjusted to 4.8 by adding 315 ml of 2.5N NaOH. The mother liquor was kept under slow stifling conditions for 15 minutes and then transferred to cold room (2-8° C.), where it was kept for five hours. Then the supernatant was separated by centrifugation. The loss in supernatant was 4%.

Optimized Precursor Crystallisation Condition with Yield:

The SP-Sepharose elution pool was chilled to 20°+5° C., 5 mL (0.5% V/V) of phenol was added for each liter of elution pool. Required amount of Phenol was added in an aliquot of elution pool and finally added to the main tank for proper redissolution. After addition of phenol the stirring was continued for some time before addition of next reagent for proper redissolution. Now, 12.5% by volume of 40 g/L Zinc chloride (4% w/v) was added to induce crystallisation. The pH was then adjusted to 4.8+0.1 using 2.5N NaOH (approx. 85-90% of SP-EP volume). This entire mixture was stirred for 30 minutes to ensure homogeneity and then held at 2-8° C. for at least 8 hours before centrifugation. Based on the loss in the supernatant, the yield was approximately 90% at this step.

Example 5

Trypsinisation

Glargine was prepared from Glargine precursor through an enzymatic conversion. The conversion was effected by the presence of trypsin or trypsin-like enzymes of plant, animal or microbial origin. The reaction was carried out preferably in presence of water-miscible organic solvents like DMSO, DMF, ethanol, acetone, acetonitrile, ethyl acetate, etc, especially DMF and DMSO. The preferable ratio of organic solvent was about 0 to 65%, especially about 40 to 60% of the reaction mixture.

The ratio of organic solvent was determined by the solubility of the starting materials, tendency of enzymes to denature and its hydrolyzing activity. Mixtures of organic solvents also can be used. The addition of organic solvents lowers the aqueous concentration of the reaction mixture, resulting in prevention of hydrolysis of product, and also remarkably increases the solubility of the products.

The concentration of the precursor was generally about 5 to 50 g/L. The reaction was carried out at about pH 5 to 12, preferably about pH 8 to 10. Reaction temperature was about 0-40° C., preferably about 2-25° C. Trishydroxylmethylaminomethane (TRIS) or other buffer systems was used at different ionic strengths to maintain the required pH. Reaction time was variable and was affected by other reaction conditions. Reaction was continued until the purity of the product starts decreasing due to the hydrolysis of the product. It takes generally about 30 minutes to 24 hours and in most cases about 4 to 10 hours.

The concentration of enzyme was determined depending on concentration of substrates and enzyme activity. For example, the crystalline trypsin available in the market was used preferably in a concentration about 10 to 100 mg/L.

Example 5a 1 g of glargine precursor was dissolved in 1.5 ml of 1M TRIS solution. 1 ml each of this solution was taken into two tubes labeled as sample A and sample B. To sample A, 3 ml of water and 166.6 mg of TRIS were added. To sample B, 2 ml of DMF, 1 ml of water and 166.6 mg of TRIS were added. Each sample was split into four by adjusting the pH to four different pH. The reaction was carried out in all the samples by adding bovine trypsin at a concentration of 50 µg/ml. The conditions tried are tabulated as follows.

TABLE 1

| SAMPLE | SOLVENT % | PH | TRIS CONCEN- TRATION (M) | TRYPSIN CONCEN- TRATION (µg/mL) | PRECURSOR CONCEN- TRATION (mg/mL) |
|---|---|---|---|---|---|
| A1 | 0% | 9.2 | 0.5 | 50 | 15.5 |
| A2 | | 8.2 | | | |
| A3 | | 7.0 | | | |
| A4 | | 6.2 | | | |
| B1 | 50% | 8.9 | | | |
| B2 | | 8.0 | | | |
| B3 | | 7.0 | | | |
| B4 | | 6.3 | | | |

All the conditions gave product at different proportions. The sample B1 gave best conversion at around 40% whereas conditions A1, A2, A3 and A4 gave less than 15% conversion. Conversions to Glargine in other samples were in the range of 15% and 40%.

Example 5b 1.6 g of Glargine precursor was dissolved in 2 ml of 1M TRIS solution. 1 ml each of this solution was taken into three tubes labeled as sample A, sample B and sample C. To sample A, 1.8 ml of water, 1.2 ml of DMF and 161 mg of TRIS were added. To sample B, 0.6 ml of water, 2.4 ml of DMF and 161 mg of TRIS were added. To sample C, 1 ml of water, 2.0 ml of DMF and 161 mg of TRIS were added. Both sample A and B were split into four and sample C into two by adjusting to different pH. The reaction was carried out in all the samples by adding bovine trypsin at a concentration of 50 µg/ml. The conditions tried were tabulated as follows.

TABLE 2

| SAMPLE | SOLVENT (DMF) % | PH | TRIS CONCEN- TRATION (M) | TRYPSIN CONCEN- TRATION (µg/mL) | PRECURSOR CONCEN- TRATION (mg/mL) |
|---|---|---|---|---|---|
| A1 | 30% | 10.1 | 0.5 | 50 | 10.5 |
| A2 | | 9.04 | | | |
| A3 | | 8.05 | | | |
| A4 | | 6.77 | | | |
| B1 | 60% | 9.95 | | | |
| B2 | | 9.13 | | | |
| B3 | | 8.01 | | | |
| B4 | | 7.0 | | | |
| C1 | 50% | 9.0 | | | |
| C2 | | 8.0 | | | |

All the conditions gave product at different proportions. The sample C1 and C2 gave best conversions at around 40% whereas other conditions gave less than 15% conversion.

Example 5c 1.5 g of Glargine precursor was dissolved in 2 ml of 1M TRIS solution. 0.75 ml each of this solution was taken into three tubes labeled as sample A, sample B and sample C. To sample A, 0.75 ml of water, 1.5 ml of ethanol and 106 mg of TRIS were added. To sample B, 0.75 ml of water, 1.5 ml of DMF and 106 mg of TRIS were added. To sample C, 0.75 ml of water, 1.5 ml of DMF and 106 mg of TRIS were added. Both samples A and B were split into two by adjusting to two different pH. The sample C was adjusted to pH 9.0. The reaction was carried out in all the samples by adding bovine trypsin at a concentration of 50 µg/ml. The conditions tried are tabulated as follows.

TABLE 3

| SAMPLE | SOLVENT % | PH | TRIS CONCEN- TRATION (M) | TRYPSIN CONCEN- TRATION (µg/mL) | PRECURSOR CONCEN- TRATION (mg/mL) |
|---|---|---|---|---|---|
| A1 | 50% | 9.0 | 0.5 | 50 | 17 |
| A2 | ETHANOL | 7.3 | | | |
| B1 | 50% | 8.9 | | | |
| B2 | DMSO | 6.9 | | | |
| C1 | 50% DMF | 9.0 | | | |

All the conditions gave product at different proportions. The sample C1 gave best conversions at around 40%, followed by B1 (~30%), whereas other conditions gave less than 15% conversion.

Example 5d 1.5 g of Glargine precursor was dissolved in 2 ml of 1M TRIS solution. 0.75 ml of this solution was taken and to this 0.75 ml of water, 1.5 ml of ethanol and 106 mg of TRIS were added. The pH was then adjusted to 9.0. Then the solution was split into two samples—A and B. For sample A, the reaction was carried out at room temperature (20 to 25° C.) whereas for sample B, the reaction was done at 2 to 8° C. Reaction was started by adding bovine trypsin at a concentration of 50 µg/ml.

Both the samples gave conversion of around 40%. The reaction at lower temperature (sample B) took longer duration but showed slightly better yield.

Example 5e 1 g of Glargine precursor was dissolved in 1 ml of 1M TRIS solution. 0.75 ml each of this solution was taken into two tubes labeled as sample A, and sample B. To sample A, 0.75 ml of water, 1.5 ml of DMF and 130 mg of TRIS were added. To sample B, 0.75 ml of water, 1.5 ml of DMSO and 130 mg of TRIS were added. Both samples A and B were split into two after adjusting to pH 8.7. The reaction was carried out in all the four samples by adding bovine trypsin at a concentration of 50 µg/ml. Reactions in one aliquot each from sample A and B were done at 2-8° C. The conditions tried are tabulated as follows.

TABLE 4

| SAMPLE | SOLVENT % | PH | TRIS CONCENTRATION (M) | TRYPSIN CONCENTRATION (µg/mL) | PRECURSOR CONCENTRATION (mg/mL) | TEMPERATURE (°C) |
|---|---|---|---|---|---|---|
| A1 (DMF) | 50% | 8.7 | 0.5 | 50 | 13.5 | 20-25 |
| A2 (DMF) | | | | | | 2-8 |
| B1 (DMSO) | | | | | | 20-25 |
| B2 (DMSO) | | | | | | 2-8 |

All the samples gave similar conversion (~40%). The reaction in samples at room temperature was over within one hour whereas those at cold room were over by 5-6 hours.

Example 5f 2 g of Glargine precursor was dissolved in a solution containing 0.5 g TRIS, 2 ml water and 2 ml DMF. From this solution, 6 samples of 3.08 ml were made such that each contained 50% DMF& 0.5M TRIS, at pH 8.7. The precursor concentration was varied among these samples from 10 g/L to 60 g/L. Reaction was started in each sample by adding 5 mg trypsin per gram of precursor. All the samples were at 2-8° C. during the reaction. The conditions tried are tabulated as follows.

TABLE 5

| SAMPLE | SOLVENT % | PH | TRIS CONCENTRATION (M) | TRYPSIN CONCENTRATION (µg/mL) | PRECURSOR CONCENTRATION (mg/mL) | TEMPERATURE (°C) |
|---|---|---|---|---|---|---|
| A | 50% | 8.7 | 0.5 | 50 | 10 | 2-8 |
| B | | | | 100 | 20 | |
| C | | | | 150 | 30 | |
| D | | | | 200 | 40 | |
| E | | | | 250 | 50 | |
| F | | | | 300 | 60 | |

All the samples were showing conversion, but samples with lower concentration gave faster reaction. condition B was considered the best. The maximum yield obtained in each case was around 40-45%. The results have been represented in FIG. 1

Optimized Process Condition with Yield and Purity

Example 5g

The wet precursor crystals were stored in −20° C. deep freezer which was taken out well before dissolution. These crystals were dissolved by adding that into a TRIS solution (TRIS—50% w/w of precursor crystals and water—2 L per kg of precursor crystals) under stirring conditions. For example, 1 kg of precursor crystal is added into 2 L TRIS solution containing 500 grams of TRIS. This was followed by addition of DMF (2 L per kg of precursor crystals). The whole mixture is completely solubilised and this solution was treated as Test solution. The resultant test solution was analyzed for product content using C18 symmetry analytical RP-HPLC method.

According to the product content in the test solution, the control solution for trypsinisation reaction was made, such that the recombinant insulin Glargine precursor concentration was 10 g/L of the reaction mixture. To prepare the control solution, the required amount of TRIS in water was added to keep the final TRIS concentration in the reaction mixture as 500 mM. This was followed by the addition of DMF such that the final DMF concentration was 50%. The temperature of this solution was then brought to 6° C.±2° C., and then the pH was adjusted to 8.7 using glacial acetic acid (around 2% of total volume) under mild stirring conditions. This solution was treated as control solution.

The reaction mixture was maintained at 6° C.±2° C. at very slow impeller speed. After complete mixing, 50 mg/L of trypsin was added to initiate the reaction. The enzyme reaction starts once the trypsin is well dissolved by mixing.

The enzyme reaction was carried out at 6° C.±2° C. at very slow impeller speed. The progress of the reaction was monitored by checking every hour, the percentage of recombinant insulin Glargine and the unreacted precursor, using the C18 Symmetry analytical RP-HPLC method. The enzyme reaction was typically completed in less than 10 hours. The reaction was stopped by adjusting the pH of the reaction mixture to 5.0 using glacial acetic acid, when the percentage of unreacted precursor was less than 5%. The reaction is expected to yield around 40% of Recombinant Insulin Glargine and purity obtained was about 35-50%.

Figure 2:
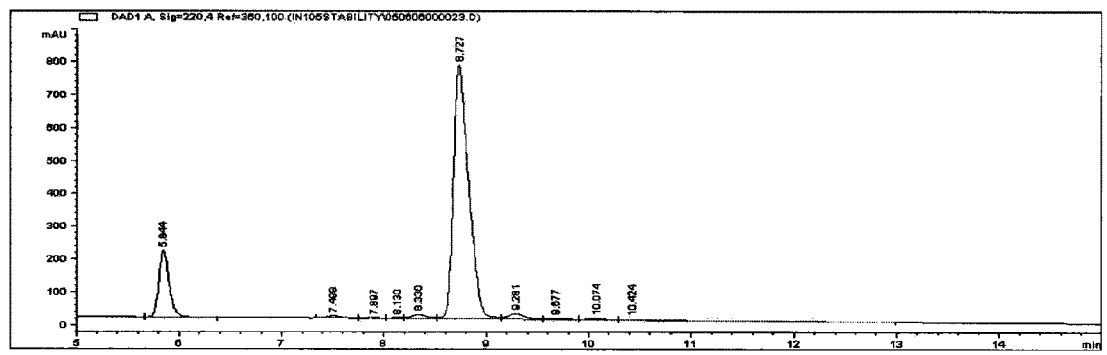
FIG. 2: Analytical Chromatogram of the reaction at different time point-before and after enzyme treatment.
Figure 2:
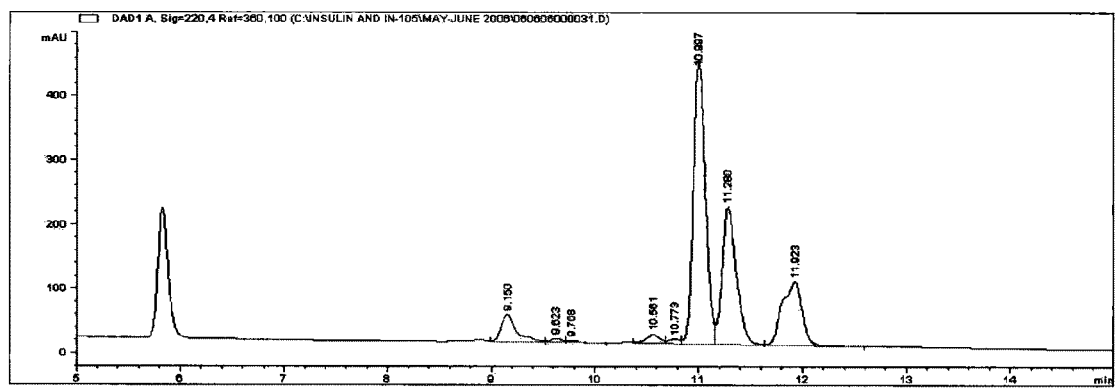
Figure 3:
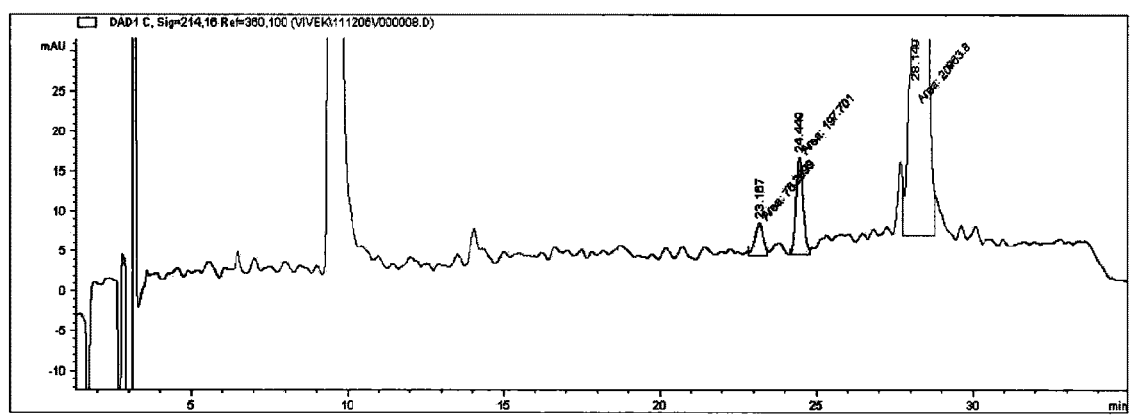
FIG. 3: HPLC profile of insulin-Glargine
Figure 4:
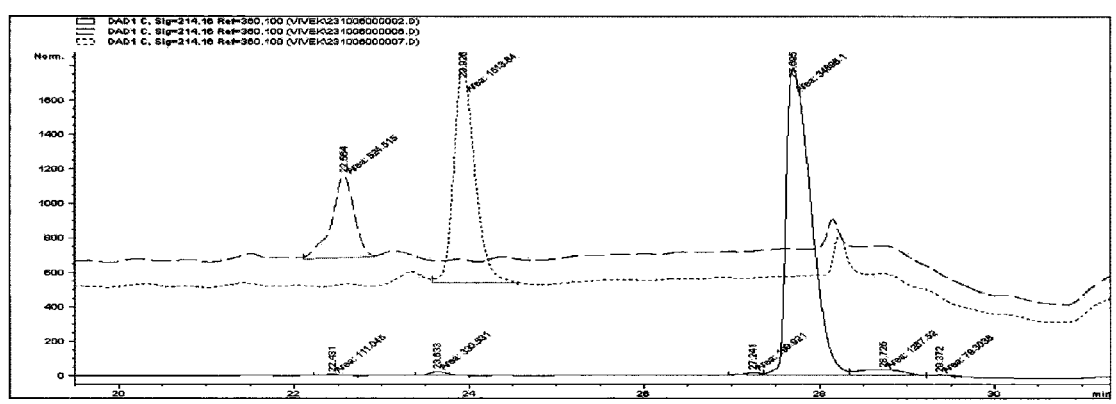
FIG. 4: Comparison of retention times of isolated impurities with final product.

Analytical chromatogram of the reaction at different time points is represented in FIGS. 2 & 3.

Example 6

RP-HPLC Purification

Example 6a

Insulin glargine precursor produced by fermentation of *Pichia pastoris* was subjected to purification, the steps involved in the process were as follows:

The column packed with SP sepharose fast flow matrix (GE Biosciences) was equilibrated with 50 mM acetic acid. The cell free supernatant adjusted to pH 3.8 using orthophosphoric acid was loaded on a cation-exchange column. The loading on the column was <50 g/L. The elution was performed using ammonium acetate. The recovery of the step was 95% at <50 g/L loading. The elution pool was crystallised. The crystal was used for trypsinisation. The column packed with RP-HPLC resin (C8 Daisogel 120 Å pore, 10 μm particle size) was equilibrated with 10% of acetonitrile (Buffer B) in 250 mM acetic acid (Buffer A). The loading of trypsinisation end diluted 1:5 using water was performed. A linear gradient of buffer B was used to elute the purified glargine at yield of 75% with purity 94.5% at a loading of <10 g/L. The column packed with RP-HPLC resin (C8 Daisogel 120 Å pore, 10 μm particle size) was equilibrated with 10% of acetonitrile (Buffer B) in 200 mM sodium acetate pH 5.0 (Buffer A). The loading of RP eluate from previous step, diluted to contain 10% acetonitrile was performed. A linear gradient of buffer B was used to elute the purified glargine at yield of 80% with purity 98.5% and glycosylated impurity of 0.29%. The column packed with RP-HPLC resin (C8 Daisogel 120 Å pore, 10 μm particle size) was equilibrated with 6% of ethanol (Buffer B) in 50 mM acetic acid (Buffer A). The loading of RP eluate from previous step, diluted to 1:3 with water, was performed. A linear gradient of buffer B was used to elute the purified glargine at yield of 85% with purity 99.4% at a loading of 35 g/L Example 6b The column packed with RP-HPLC resin (C8 Daisogel 120 Å pore, 10 μm particle size) was equilibrated with 10% of acetonitrile (Buffer B) in 250 mM acetic acid (Buffer A). The loading of, trypsinisation end diluted 1:5 using water, was performed. A linear gradient of buffer B was used to elute the purified glargine at yield of 75% with purity 94.5% at a loading of <10 g/L. The column packed with RP-HPLC resin (C8 Daisogel 120 Å pore, 10 μm particle size) was equilibrated with 10% of acetonitrile (Buffer B) in 200 mM sodium acetate pH 5.0 (Buffer A). The loading of RP eluate from previous step, diluted to contain 10% acetonitrile, was performed. A linear gradient of buffer B was used to elute the purified glargine at yield of 80% with purity 98.5% and glycosylated impurity of 0.29%. The column packed with RP-HPLC resin (C8 Daisogel 120 Å pore, 10 μm particle size) was equilibrated with 6% of ethanol (Buffer B) in 10 mM citric acid (Buffer A). The loading of RP eluate from previous step, diluted to 1:3 with water, was performed. A linear radiant of buffer B was used to elute the purified glargine at yield of 79.2% with purity 98.5% at a loading of 35 g/L.

Example 6c

The column packed with RP-HPLC resin (C8 Daisogel 120 Å pore, 10 μm particle size) was equilibrated with 10% of acetonitrile (Buffer B) in 250 mM acetic acid (Buffer A). The loading of, trypsinisation end diluted 1:5 using water was performed. A linear gradient of buffer B was used to elute the purified glargine at yield of 75% with purity 94.5% at a loading of <10 g/L. The column packed with RP-HPLC resin (C8 Daisogel 120 Å pore, 10 μm particle size) was equilibrated with 10% of acetonitrile (Buffer B) in 100 mM Tris+20 mM CaCl2 pH 8.5 (Buffer A). The loading of RP eluate from previous step, diluted to contain 10% acetonitrile, was performed. A linear gradient of buffer B was used to elute the purified glargine at yield of 71% with purity 97.4% and glycosylated impurity of 0.22%. The column packed with RP-HPLC resin (C8 Daisogel 120 Å pore, 10 μm particle size) was equilibrated with 6% of ethanol (Buffer B) in 10 mM citric acid (Buffer A). The loading of RP eluate from previous step, diluted to 1:3 with water, was performed. A linear gradient of buffer B was used to elute the purified glargine at yield of 75.0% with purity 98.0% at a loading of 35 g/L.

Example 6d

The column packed with RP-HPLC resin (C8 Daisogel 120 Å pore, 10 μm particle size) is equilibrated with 10% of acetonitrile (Buffer B) in 250 mM acetic acid (Buffer A). The loading of, trypsinisation end diluted 1:5 using water, is performed. A linear gradient of buffer B is used to elute the purified glargine at yield of 75% with purity 94.5% at a loading of <10 g/L. The column packed with RP-HPLC resin (C8 Daisogel 120 Å pore, 10 μm particle size) is equilibrated with 10% of acetonitrile (Buffer B) in 100 mM ammonium acetate pH 5.0 (Buffer A). The loading of RP eluate from previous step, diluted to contain 10% acetonitrile, is performed. A linear gradient of buffer B is used to elute the purified glargine at yield of 60.7% with purity 98.0% and glycosylated impurity of 0.91%. The column packed with RP-HPLC resin (C8 Daisogel 120 Å pore, 10 μm particle size) is equilibrated with 6% of ethanol (Buffer B) in 10 mM citric acid (Buffer A). The loading of RP eluate from previous step, diluted to 1:3 with water, is performed. A linear gradient of buffer B is used to elute the purified glargine at yield of 75.0% with purity 98.5% at a loading of 35 g/L.

Example 6e

The column packed with RP-HPLC resin (C8 Daisogel 120 Å pore, 10 μm particle size) was equilibrated with 10% of acetonitrile (Buffer B) in 250 mM acetic acid (Buffer A). The loading of, trypsinisation end diluted 1:5 using water, was performed. A linear gradient of buffer B was used to elute the purified glargine at yield of 75% with purity 94.5% at a loading of <10 g/L. The column packed with RP-HPLC resin (C8 Daisogel 120 Å pore, 10 μm particle size) was equilibrated with 10% of acetonitrile (Buffer B) in 20 mM perchloric acid pH 3.0 (Buffer A). The loading of RP eluate from previous step, diluted to contain 10% acetonitrile, was performed. A linear gradient of buffer B was used to elute the purified glargine at yield of 37.4% with purity 96.2% and glycosylated impurity of 0.28%. The column packed with RP-HPLC resin (C8 Daisogel 120 Å pore, 10 μm particle size) was equilibrated with 6% of ethanol (Buffer B) in 10 mM citric acid (Buffer A). The loading of RP eluate from previous step, diluted to 1:3 with water, was performed. A linear gradient of buffer B was used to elute the purified glargine at yield of 70.0% with purity 97.0% at a loading of 35 g/L Example 6f The column packed with RP-HPLC resin (C8 Daisogel 120 Å pore, 10 μm particle size) was equilibrated with 10% of acetonitrile (Buffer B) in 250 mM acetic acid (Buffer A). The loading of, trypsinisation end diluted 1:5 using water, was performed. A linear gradient of buffer B was used to elute the purified glargine at yield of 75% with purity 94.5% at a loading of <10 g/L. The column packed with RP-HPLC resin (C8 Daisogel 120 Å pore, 10 μm particle size) was equilibrated with 10% of acetonitrile (Buffer B) in 100 mM Borate buffer pH 8.5 (Buffer A). The loading of RP eluate from previous step, diluted to contain 10% acetonitrile, was performed. A linear gradient of buffer B was used to elute the purified glargine at yield of 79.4% with purity 98.3% and glycosylated impurity of 0.11%. The column packed with RP-HPLC resin (C8 Daisogel 120 Å pore, 10 μm particle size) was equilibrated with 6% of ethanol (Buffer B) in 10 mM citric acid (Buffer A). The loading of RP eluate from previous step, diluted to 1:3 with water, was performed. A linear gradient of buffer B was used to elute the purified glargine at yield of 75.0% with purity 98.8% at a loading of 35 g/L.

Example 7

Final Precipitation

The glargine purified through different reverse phase chromatography steps was precipitated by adding citric acid buffer and ZnCl2 solution, and adjusting the pH. (The citric acid buffer comprises 15.4 g/L citric acid (anhydrous), 90 g/L di-sodium orthophosphate (anhydrous) buffer, pH adjusted to 6.3.+0.1, with o-phosphoric acid). The precipitation was done at a pH range of 4.0 to 10.0, preferably 6.0 to 8.0. The product concentration was preferably 2-20 g/L. After the precipitation, the product was separated from the clear supernatant by either centrifuging or decanting the supernatant without disturbing the settled precipitate. The precipitate so obtained was washed with chilled water to remove the unbound ions present.

The yield of the whole process was 85-90% and the product purity was around 99%.

Example 8

The final suspension was decanted after settling and the slurry was transferred aseptically to the freeze dryer trays. The slurry was then frozen and lyophilized to get dry powder of Insulin Glargine, which can be stored and formulated later.

Example 9

Isolation and Characterization of the Glycosylated Impurity

Isolation of Glycoforms of Glargine from In-House Active Pharmaceutical Ingredient

Example 9a

To characterise glycoforms of impurities mGIG (monoglycosylated insulin glargine) and tGIG (triglycosylated insulin glargine) were isolated by semi-preparative reverse phase chromatography. Identification of process impurities were carried out on an Agilent 1100 chromatography system (CA, USA) using a Prochrome C18 (250×8.0 mm) column. The mobile phase solvents were aqueous 0.1% TFA (A) and 0.1% TFA in acetonitrile (B). Impurities of glargine were eluted using a linear gradient program: 0 min 25% B; 0-10 min 27% B; 10-15 min 29% B; 15-21 min 30% B; 21-27 min 33% B and 27-35 min 25% B at a constant flow rate of 1.5 mLmin-1. The injection volume was kept at 20 µl and column temperature was maintained at 40° C. The eluants were monitored at 214 nm. The chromatographic peaks corresponding to glycosylated impurities were analysed online by Agilent 1100 series LCMSD SL ion trap mass spectrometer (Agilent Technologies, USA). The mass spectrometer was operated in ESI mode. The nebuliser gas was kept at 60 psi, drying gas at 12.0 L min-1 and drying temperature was kept at 350° C. Positive ion electrospray mass spectrum was recorded in MS mode in the mass range 600-2200 m/z.

The peaks corresponding to mGIG and tGIG were manually collected. Since mGIG (1.0%) and tGIG (0.3%) were observed at trace level in formulations, Glargine active pharmaceutical ingredient (API) of the subject invention was used at a concentration 100 mg mL-1 for purifying process impurities.

Characterization of the Final Purified Product

Example 9b

RP-HPLC and SEC-HPLC Profiles of the Final Product

Figure 5:
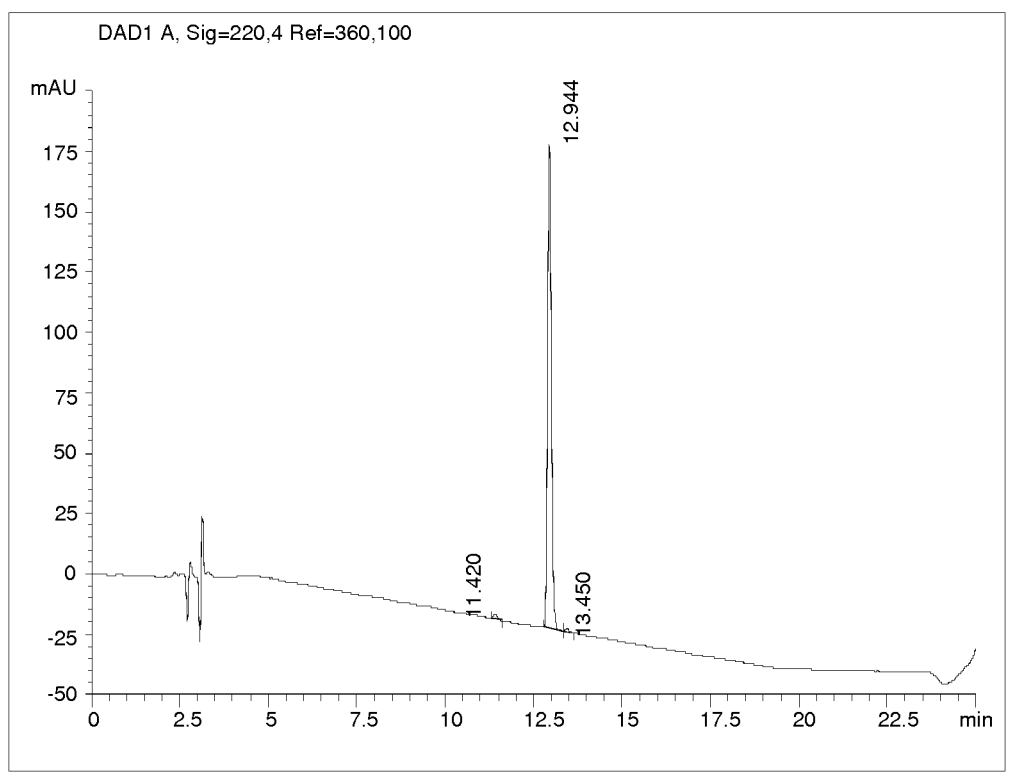
FIG. 5: RP-HPLC profile of the Insulin-glargine final product.
Figure 6:
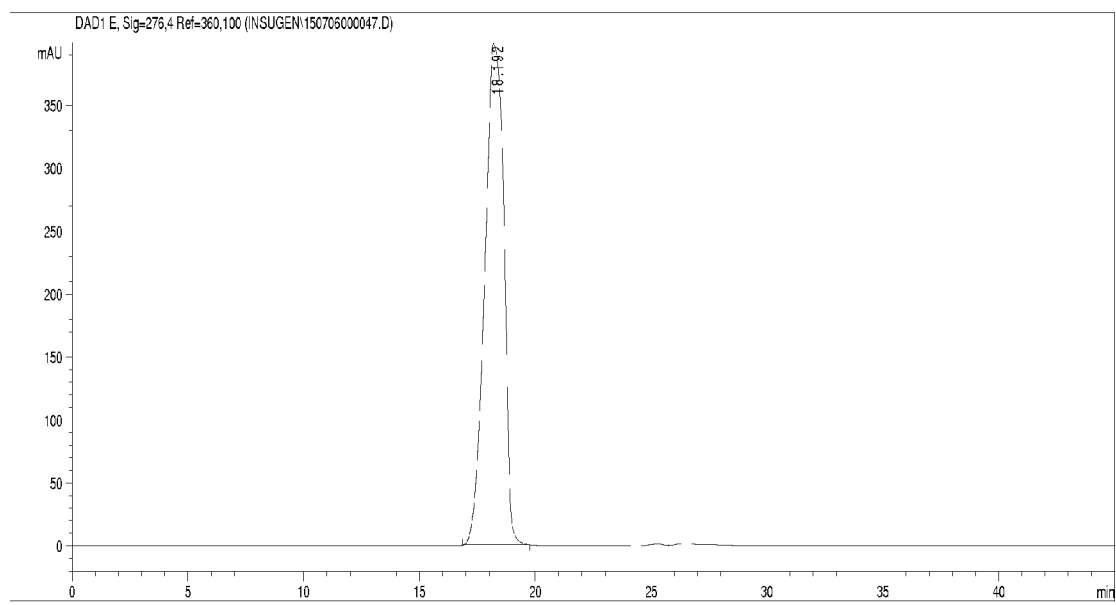
FIG. 6: SEC-HPLC profile of the insulin glargine final product.

The RP-HPLC profile and the SEC-HPLC profile of the final protein product obtained has been represented in FIG. 5 and FIG. 6.

Example 9c

Figure 7:
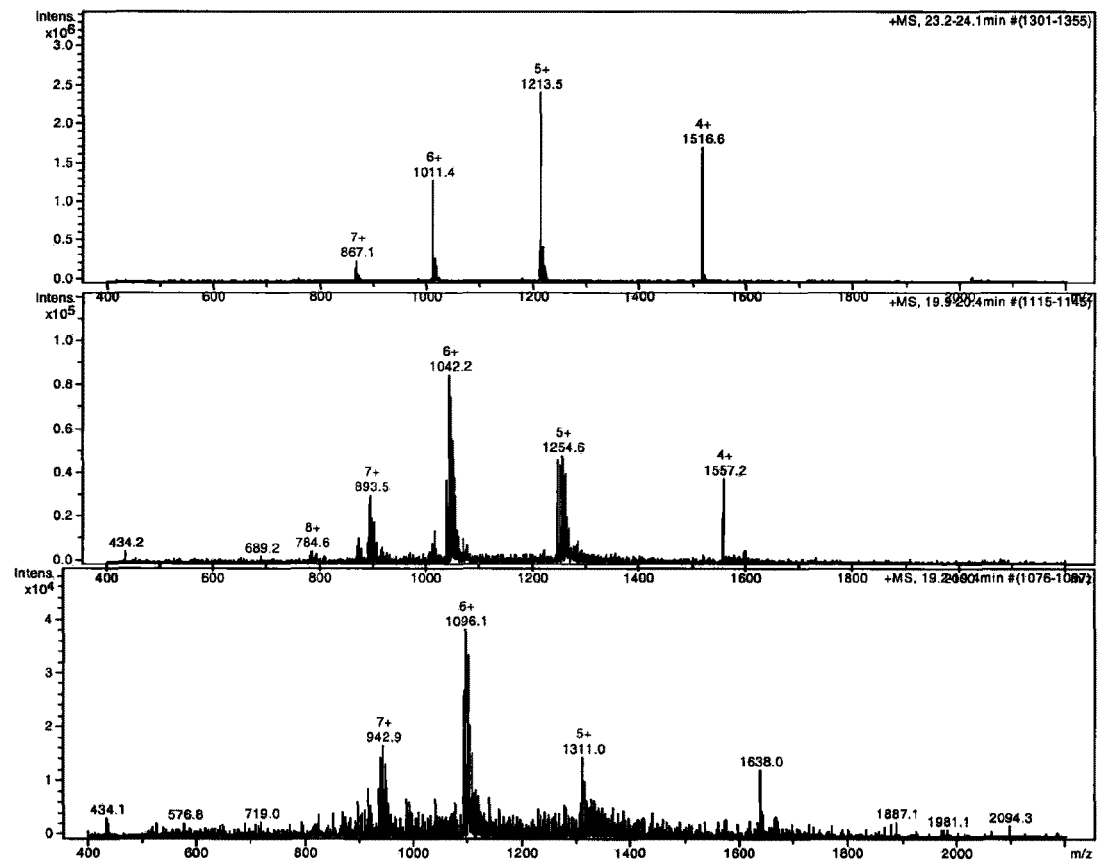
FIG. 7: Electrospray ionisation mass spectra of glargine, monoglycosylated insulin glargine (mGIG) and triglycosylated (tGIG).
Figure 8:
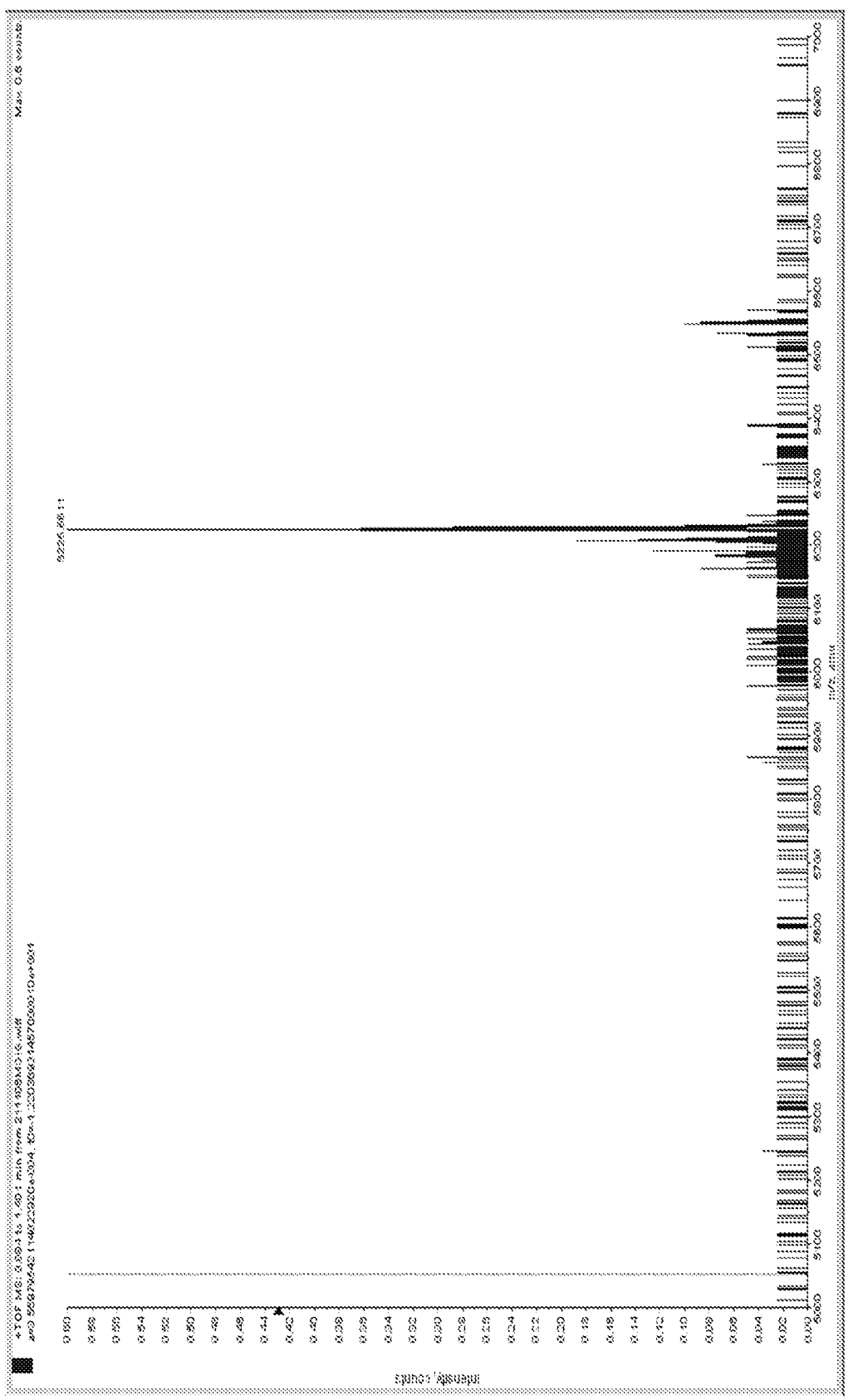
FIG. 8: Matrix assisted laser desorption ionisation mass spectrum of monoglycosylated insulin glargine (mGIG)
Figure 9:
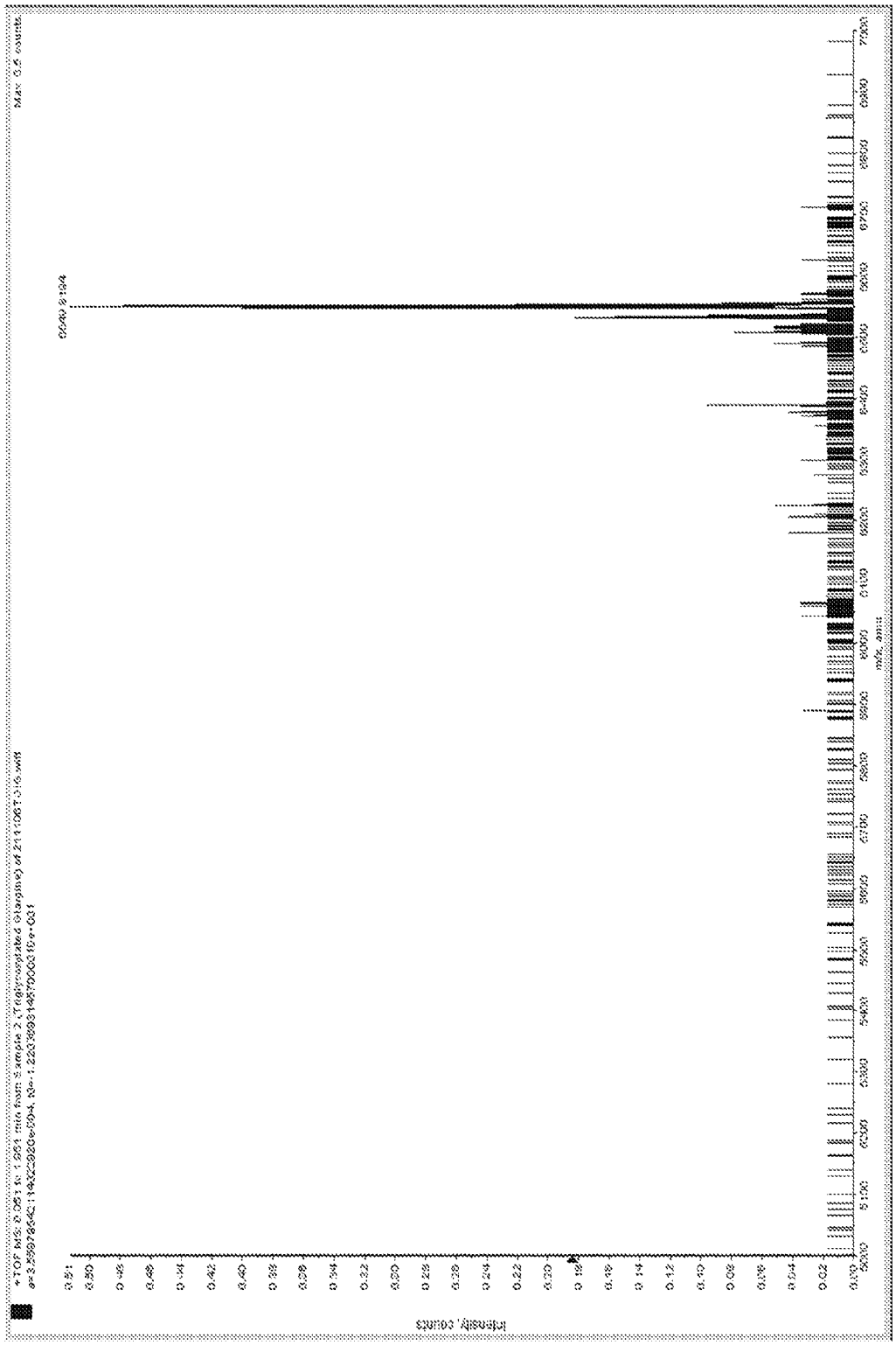
FIG. 9: Matrix assisted laser desorption ionisation mass spectrum of triglycosylated glargine (tGIG)

Electrospray ionization mass spectra of glargine, monoglycosylated insulin glargine (mGIG) and tri-glycosylated insulin glargine (tGIG) are represented in FIG. 7, FIG. 8 and FIG. 9 respectively.

| Sample | Time | Area | Height | Width | Area % | Symmetry |
|---|---|---|---|---|---|---|
| Batch No. 1 | 18.192 | 190417 | 399.4 | 0.9616 | 100 | 0.881 |

Introduction of one monosaccharide unit to glargine decrease the retention time due to increase in polarity and increase in mass unit of 162 units; similarly introduction of three monosaccharides further increase in polarity and increase in mass of 486 units. The molecular weights of glycoforms were obtained by deconvoluting multiply charged peaks in ESI-MS.

TABLE 6

Comparisons of molecular weight observed by electrospray and matrix assisted laser desorption ionization techniques.

| | MOLECULAR WEIGHT | |
|---|---|---|
| | ESI | MALDI |
| Insulin Glargine | 6063.2 | 6063.4 |
| mGIG | 6225.7 | 6225.6 |
| tGIG | 6549.4 | 6549.8 |

MALDI mass spectra obtained for mGIG and tGIG showed molecular weights 6225.6 and 6549.8 respectively. The molecular weight data observed for mGIG and tGIG are consistent with data observed by ESI-MS. The molecular weight difference between IG, mGIG and tGIG showed multiples of 162 mass units suggesting that glycans are covalently attached to glargine.

FIG. 8. Matrix assisted laser desorption ionisation mass spectrum of monoglycosylated insulin glargine (mGIG)

Reduction and alkylation experiments were undertaken to identify the chain at which glycosylation had taken place. The method was standardised using glargine as standard. 1.1 mg of glargine was dissolved in 500 µl of 8M guanidine HCl, 0.1M TRIS and 1 mM EDTA buffer maintained at a pH of 9.0. To this 10 µl of 1M dithiothreitol (DTT) was added. The contents were mixed and incubated at 37° C. for 2 hrs. The incubated samples were brought to room temperature and 10 µl of iodoacetamide was added. The samples were covered in aluminium foil to protect from light, incubated at 37° C. for two hours and analysed by LCMS. In a similar way mGIG and tGIG was reduced and alkylated for the identification of glycosylation.

TABLE 7

Reduction and Alkylation of Glycosylated Glargines done to identify chains at which glycosylation taken place

|  | Intact RT* (Min) | Intact Mass (m/z) | Chain A Retention Time* (Min) | Chain A Mass (m/z) | Chain B Retention Time (Min) | Chain B Mass (m/z) |
|---|---|---|---|---|---|---|
| Glargine | 27.5 | 6063 | 5.5 | 2555 | 20.5 | 3857 |
| Mono Glycosylated Glargine | 23.4 | 6225 | 5.2 | 2718 | 21.3 | 3857 |
| Tri Glycosylated Glargine | 22.2 | 6549 | 5.2 | 2718 | 20.1 | 4180 |

Example 9d

Peptide Mapping

The glycoforms of glargine were subjected to enzyme digestion to identify the amino acid position at which the glycosylation had taken place. 0.65 mg of native glargine dissolved in 200 μl of 1M TRIS (pH=9.0). To this freshly prepared 50 μl of 1 mg mL-1 of V 8 protease (Glu-C) was added and incubated at 37° C. for two hours. The tryptic digest of IG, mGIG and tGIG were separated on a C18 250× 4.6 mm, 5μ, 300° (Waters; symmetry) at a flow rate of 0.8 mL min-1. The column temperature was maintained at 40° C. The following gradient was used 0-60 min, 5-80% B, 60-65 min, 80-5% B. Solvent A=0.1% aqueous TFA and solvent B=Acetonitrile. 20 μl of sample was injected and eluted peaks were monitored at 220 nm. The samples were analysed online by Agilent 1100 LCMS for GLU-C fragments analysis. A comparative study was done for IG, mGIG and tGIG to find out the difference in retention time and molecular masses.

TABLE 8

Comparison of intact, fragments retention times and masses of glycosylated glargine:

|  |  | Retention time | Molecular Mass |
|---|---|---|---|
| Intact | Glargine | 27.9 | 6063 |
|  | mGIG | 26.8 | 6225 |
|  | tGIG | 26.5 | 6549 |
| A1-A4 | Glargine | 10.3 | 417 |
|  | mGIG | 11.3 | 417 |
|  | tGIG | 12.3 | 417 |
| B22-B32 | Glargine | 17.4 | 1428 |
|  | mGIG | 17.5 | 1428 |
|  | tGIG | 16.9 | 1752 |
| B14-B21 | Glargine | 20.3 | 1320 |
| A18-A21 | mGIG | 20.3 | 1320 |
|  | tGIG | 20.3 | 1320 |
| B1-B13 | Glargine | 23.2 | 2970 |
| A5-A17 | mGIG | 22.5 | 3132 |
|  | tGIG | 22.6 | 3132 |

SUMMARY OF THE INVENTION

The present invention aims to provide a method of producing and purifying recombinant protein which encodes a polypeptide displaying immunological and biological activities of mature insulin glargine. The said purified protein is found to have all physiological, immunological and biochemical characteristics similar to mature insulin glargine.

Another preferred aspect of the present invention is characterisation of the glycosylated impurities of glargine obtained in the final product.

The final and the most significant objective of the present invention is to obtain the insulin glargine protein in a pure form. The invention thus permits simple large scale production and subsequent purification of insulin glargine.

An object of the present invention is therefore constituted by an improved method for the preparation of insulin glargine in the pure form.

According to the first aspect of the invention, the recombinant method of producing insulin glargine comprises:

(a) Preparation of a DNA sequence capable of directing a host microorganism to produce a protein having insulin glargine activity;

(b) Cloning the said DNA sequence into a vector capable of being transferred into and replicating in a host microorganism, such vector containing operational elements for the DNA sequence;

(c) Transferring the vector containing the DNA sequence and operational elements into a host microorganism capable of expressing the insulin glargine protein;

(d) Culturing the microorganism under conditions appropriate for amplification of the vector and expression of the protein;

(e) Harvesting the protein.

The second aspect of the invention features a method for constructing the recombinant vector carrying the gene of interest including the steps of cloning the insulin glargine precursor gene in frame with a signal peptide in an suitable expression vector, transforming the host cell with the vector harboring the recombinant gene of interest, screening for multi-copy integrants, selection of the recombinant clones with successful integration of insulin glargine precursor in the genome.

The third aspect of the invention relates to small scale expression of the insulin glargine precursor for the HPLC analysis for detecting the expression level of the desired protein of interest.

The fourth aspect of the invention relates to the fermentation process including steps of growing recombinant cells in a growth medium, the cells being a microorganism or cell culture transformed with an expression vector containing DNA encoding the desired protein, which in case of the instant invention is insulin glargine.

The fifth aspect of the invention is directed to crystallisation of the insulin glargine product produced post fermentation.

The sixth aspect of the invention is related to the trypsinisation process. Glargine can be prepared from the Glargine precursor through an enzymatic conversion. The conversion is effected by the presence of trypsin or trypsin like enzymes of plant, animal or microbial origin.

A significant aspect of the present invention relates to processes and procedures useful in purifying the protein isolated having biological activities similar to that of the natural insulin glargine protein; and more particularly, to processes which utilize RP-HPLC or other chromatography methods for separating the active peptide substance from other substances which do not have such activity and so may be regarded as impurities.

The most preferred aspect of the invention relates to the identification of various glycoforms of insulin analogues more specifically insulin glargine through chemical methods coupled with mass spectrometry techniques such as electrospray and matrix assisted laser desorption ionisation for identification. The invention shall herewith permit selective purification of the product from the aforesaid impurities through optimised down stream purification methods attributed to the better understanding of the nature of impurities present in the final product.

Additional objects and advantages of the invention will be set forth in part in the description which follows, and in part will be obvious from the description or may be learned from practice of the invention. The objects and advantages may be realised and attained by means of the instrumentalities and combinations particularly pointed out in the appended claims. The present invention relates to a method of obtaining a purified, biologically active heterologous protein.

The accompanying drawings, which are incorporated herein and constitute a part of this application, illustrate various attributes useful in this invention and, together with the description, serve to explain the principles of the invention.

We claim:

1. A process of obtaining a recombinant insulin glargine having purity of at least 96% and containing less than 1% glycosylated impurity by a yeast expression system, said process comprising steps of:
    a) culturing *Pichia pastoris* transformed by a vector containing a DNA sequence defined by formula X—B—Y-A encoding insulin glargine precursor wherein,
        X is a leader peptide sequence comprising at least one amino acid,
        B is the amino acid sequence of the B chain of the insulin molecule, its derivatives or analogs,
        Y is a linker peptide of amino acid sequence set forth as SEQ ID NO. 3,
        A is the amino acid sequence of the A chain of the insulin molecule, its derivatives or analogs,
        and the A and B chain can be modified by amino acid substitution, deletion and/or addition;
    b) recovering the yeast expressed insulin glargine precursor, said recovering comprises separating the insulin glargine precursor from the yeast to obtain a recovered insulin glargine precursor preparation;
    c) optionally subjecting the recovered preparation of step (b) to a step of crystallization,
    d) subjecting the recovered preparation of step (b) or crystals of step (c) to enzymatic conversion at pH ranging from about 6 to about 10, in presence of trypsin or trypsin like enzyme and water miscible organic solvent in the concentration ranging from about 40% to about 60%, to obtain insulin glargine containing at least one related impurity;
    e) purifying said insulin glargine containing at least one related impurity, said purifying comprises contacting the said insulin glargine with a RP-HPLC chromatographic matrix wherein multiple purification steps are carried out by employing:
        i) a first step of equilibrating the matrix with acetonitrile at a concentration of about 10%, in acetic acid at a concentration of about 250 mM; followed by eluting the said insulin glargine with said acetonitrile;
        ii) a second step of re-equilibrating the matrix with acetonitrile at a concentration of about 10%, in an organic acid buffer A at concentration ranging from about 20 mM to about 200 mM at pH ranging from about 3 to about 8.5, and re-eluting the said insulin glargine with said acetonitrile; and
        iii) a third step of re-equilibrating the matrix with ethanol at a concentration of about 6%, in an organic acid buffer A at concentration ranging from about 10 mM to about 50 mM; and re-eluting the said insulin glargine with said ethanol; and
    f) precipitating the purified insulin glargine of step (e) by adding a combination of citric acid buffer and zinc chloride at pH ranging from about 6 to about 8 to obtain the insulin glargine having purity of at least 96% and containing less than 1% glycosylated impurity.

2. The process according to claim 1, wherein the recovering of the insulin glargine precursor is carried out by ion-exchange chromatography.

3. The process according to claim 1, wherein the crystallization is carried out by addition of zinc chloride and phenol at a pH ranging from about 3 to about 8 and at a temperature ranging from about 2° C. to about 30° C.; and wherein the enzymatic conversion is carried out by trypsin in a water-miscible organic solvent at a pH ranging from about 8 to about 10 and at a temperature ranging from about 2° C. to about 25° C., and wherein the water-miscible organic solvent is selected from a group consisting of DMSO, DMF, ethanol, acetone, acetonitrile, ethyl acetate and mixtures thereof.

4. The process according to claim 3, wherein the crystallization is carried out at a pH ranging from about 4 to about 6.

5. The process according to claim 1, wherein the purification is carried out by RP-HPLC;
    and wherein the organic acid buffer is selected from the group consisting of citric acid, acetic acid, boric acid, formic acid, hydrochloric acid and phosphoric acid.

6. The process according to claim 1, wherein said insulin glargine is defined by polypeptide sequence set forth as SEQ ID NO.: 1 or SEQ ID NO.: 2.

7. The process according to claim 6, wherein DNA sequence encoding the insulin glargine precursor defined by polypeptide sequence set forth as SEQ ID NO.: 1 or 2 is cloned in frame with a signal peptide and wherein the signal peptide is cloned in frame with-mat-α-signal peptide.

8. The process according to claim 1, wherein the *Pichia pastoris* strain is GS115.

9. The process according to claim 1, wherein glycosylated form of the insulin glargine is monoglycosylated, triglycosylated or polyglycosylated.

* * * * *

UNITED STATES PATENT AND TRADEMARK OFFICE
CERTIFICATE OF CORRECTION

PATENT NO. : 8,802,816 B2
APPLICATION NO. : 12/918079
DATED : August 12, 2014
INVENTOR(S) : Hazra et al.

It is certified that error appears in the above-identified patent and that said Letters Patent is hereby corrected as shown below:

In the Specification

In column 9, line 28, delete "Eucaryotic" and insert --Eukaryotic--, therefor

In column 10, line 20, delete "glycosyalated" and insert --glycosylated--, therefor In column 12, line 67, after "purifications", insert --.--, therefor In column 15, line 67, delete "stifling" and insert --stirring--, therefor In column 16, line 14, delete "stifling" and insert --stirring--, therefor Signed and Sealed this
Twenty-eighth Day of October, 2014

Michelle K. Lee
*Deputy Director of the United States Patent and Trademark Office*

```
SEQUENCE LISTING

<160> NUMBER OF SEQ ID NOS: 3

<210> SEQ ID NO 1
<211> LENGTH: 53
<212> TYPE: PRT
<213> ORGANISM: Artificial Sequence
<220> FEATURE:
<223> OTHER INFORMATION: Codon optimized glargine precursor sequence
<220> FEATURE:
<221> NAME/KEY: PEPTIDE
<222> LOCATION: (1)..(53)

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Gly Ile Val Glu Gln Cys Cys Thr Ser Ile Cys Ser Leu Tyr Gln Leu
            35                  40                  45

Glu Asn Tyr Cys Gly
        50

<210> SEQ ID NO 2
<211> LENGTH: 57
<212> TYPE: PRT
<213> ORGANISM: Artificial Sequence
<220> FEATURE:
<223> OTHER INFORMATION: Codon optimized Glargine Precursor sequence
<220> FEATURE:
<221> NAME/KEY: PEPTIDE
<222> LOCATION: (1)..(57)

<400> SEQUENCE: 2

Gly Ala Val Arg Phe Val Asn Gln His Leu Cys Gly Ser His Leu Val
1               5                   10                  15

Glu Ala Leu Tyr Leu Val Cys Gly Glu Arg Gly Phe Phe Tyr Thr Pro
                20                  25                  30

Lys Thr Arg Arg Gly Ile Val Glu Gln Cys Cys Thr Ser Ile Cys Ser
            35                  40                  45

Leu Tyr Gln Leu Glu Asn Tyr Cys Gly
        50                  55

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: Peptide
<222> LOCATION: (1)..(7)

<400> SEQUENCE: 3

Arg Arg Asp Ala Asp Asp Arg
1               5
```